United States Patent [19]

Inada et al.

[11] Patent Number: 4,714,791

[45] Date of Patent: Dec. 22, 1987

[54] PROCESS FOR RECOVERING PRIMARY NORMAL ALIPHATIC HIGHER ALCOHOLS

[75] Inventors: Shoshichiro Inada, Amagasaki; Kurune Furukawa, Kyoto; Takachika Masui, Hirakata; Keijiro Honda, Kagoshima; Joji Ogasawara, Kobe; Giichi Tsubakimoto, Kakogawa, all of Japan

[73] Assignees: Seitetsu Kagaku Co., Ltd.; Shinko Seito Co., Ltd.; Shinko Sugar Production Co., Ltd., all of Japan

[21] Appl. No.: 864,246

[22] Filed: May 19, 1986

[30] Foreign Application Priority Data

May 31, 1985 [JP] Japan .................................. 60-119514

[51] Int. Cl.$^4$ ................... C07C 29/76; C07C 31/125; C07C 31/02
[52] U.S. Cl. ..................................................... 568/913
[58] Field of Search ........................................ 568/913

[56] References Cited

U.S. PATENT DOCUMENTS 3,372,203  3/1968  Wimberley ........................... 568/913

3,969,196  7/1976  Zosel ..................................... 203/49

FOREIGN PATENT DOCUMENTS 494985  11/1938  United Kingdom ................ 568/913

OTHER PUBLICATIONS

Meade et al., "Cane Sugar Handbook", 10th ed. (1977), pp. 70-77, 96, 97, 152-155, 176 and 177.

Primary Examiner—J. E. Evans
Attorney, Agent, or Firm—Pollock, Vande Sande & Priddy

[57] ABSTRACT

Primary normal aliphatic higher alcohols are selectively recovered with a high efficiency by contacting sugarcanes, or products obtained from the sugarcanes, or processed products from production of sugar as an extraction raw material with a fluid in a subcritical or supercritical state as an extractant, thereby extracting a trace amount of primary normal aliphatic higher alcohols contained in the extraction raw materials as an extract and separating the extracted alcohols from the extract.

15 Claims, 1 Drawing Figure

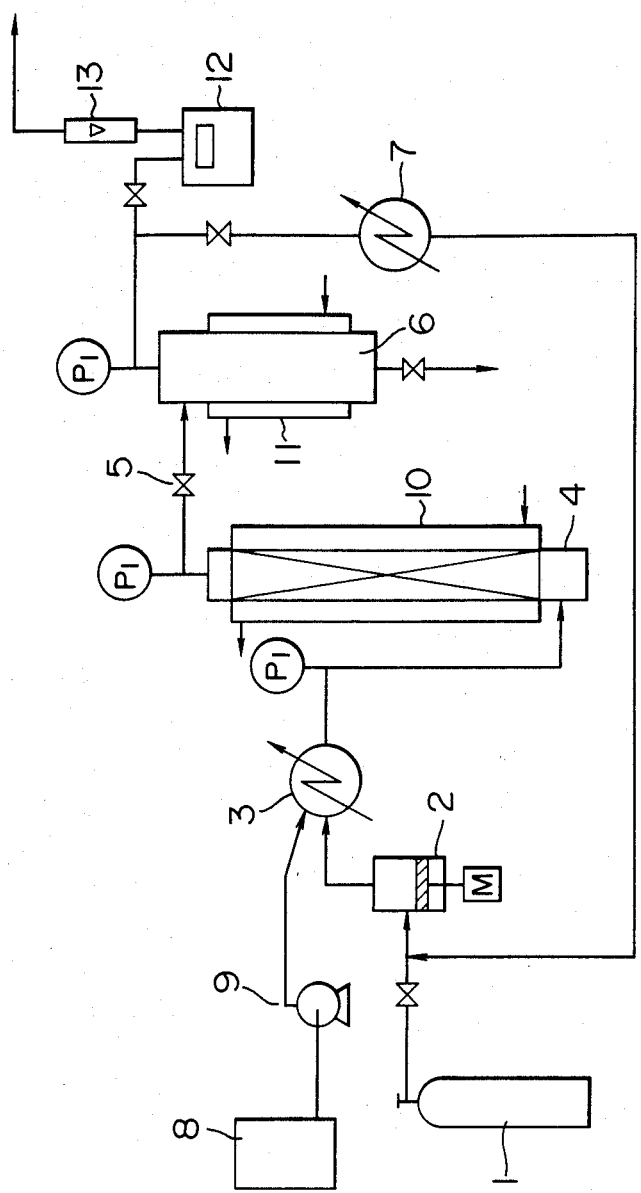
FIG.

PROCESS FOR RECOVERING PRIMARY NORMAL ALIPHATIC HIGHER ALCOHOLS

BACKGROUND OF THE INVENTION

This invention relates to a process for recovering primary normal aliphatic higher alcohols from sugarcane, or products obtained from the sugarcane, or processed products from production of sugar, more particularly by extraction using a fluid in a subcritical or supercritical state as an extractant.

Among primary normal aliphatic higher alcohols, octacosanol of $C_{28}$ and triacontanol of $C_{30}$ are important from the viewpoint of utility. Octacosanol is a linear saturated monohydric alcohol represented by the molecular formula $CH_3(CH_2)_{26}CH_2OH$ with the molecular weight of 410.74 and the melting point of 83.2° to 83.4° C. in a white crystalline state and exists as one component of vegetable wax, such as extracted from wheat blades, wax covering the rinds of apples, candelilla wax, cotton wax, etc. in the nature, and also widely distributes in vegetable oils, cereals, nuts, leaves and steams of plants, rinds of fruits, etc., but its content is a trace amount, for example, an order of 10 to 20 ppm.

It is known that octacosanol has two major effects, i.e. increase in physical stamina and remedy of damaged nerve cells, and also has the following particular functions and effects:

(1) Increase in endurance, vitality and physical stamina,
(2) Improvement of reflect action and quick action,
(3) Increase in resistance to stress,
(4) Stimulation of sex hormone and decrease in myospasm,
(5) Improvement in functions of muscles including myocardium,
(6) Decrease in systolic blood pressure, and
(7) Increase in basal metabolism.

Octacosanol is thus used in health food or for therapeutic purpose. It is appropriate to administer 1 mg/day for the ordinary increase in physical stamina, but it is better for the therapeutic purpose to administer about 40 mg/day through addition thereof to minerals or vitamins.

Triacontanol is also called melissyl alcohol and is a linear saturated monohydric alcohol represented by the molecular formula $CH_3(CH_2)_{28}CH_2OH$ with the molecular weight of 438.80 and the melting point of 86.5° C. in a white crystalline state. Triacontanol as well as octacosanol is contained in trace amount as one component of vegetable wax in the nature. It is known that triacontanol has the similar effects to those of octacosanol, and further a very remarkable effect on plant growth.

Such useful octacosanol can be obtained by chemical synthesis from behenic acid $CH_3(CH_2)_{20}COOH$ as a starting material, by electrochemical reaction of 1,18-octadecane-dicarboxylic acid monoethyl ester obtained from cyclohexane and butadiene with capric acid, or by extraction from natural vegetable oil, wax, etc.

Among natural vegetable oil, wax, etc., it is known that wheat germ oil contains about 100 ppm of octacosanol, and thus is said to be most suitable raw material for commercial scale extraction owing to its high content.

Triacontanol can be synthesized by the same electrochemical reaction as used to synthesize octacosanol, using lauric acid in place of capric acid. However, no commercial scale extraction of triacontanol from vegetable wax has been carried out yet.

Chemically synthesized octacosanol seems to have the same effect as the natural octacosanol, but it is difficult to obtain behenic acid itself as a raw material for the synthesis, and also the electrochemical procedure involves complicated synthesis step and purification step, leading to a higher cost. Furthermore, chemically synthesized octacosanol still has a fear of adverse effect on human bodies in administration because of chemically synthesized product.

Natural octacosanol is contained as much as 100 ppm in the wheat germ oil which is said to have the highest content, and only a trace amount of octacosonal is contained in other natural vegetable materials. Furthermore, octacosanol is insoluble in water, and also has a low solubility in organic solvents. That is, its extraction is very difficult to carry out and is very expensive. This is also substantially true of triaconstanol.

Separation of organic compounds from their mixtures with a fluid in a subcritical or supercritical state is disclosed, for example, in Japanese Patent Publication No. 54-10539 (=U.S. Pat. No. 3,969,196).

The fluid in a subcritical or supercritical state is a fluid approximately at the critical temperature and a critical pressure or at higher temperature and pressure than the critical temperature and critical pressure. For example, it is a fluid approximately in a critical state or supercritical state such as ethylene around 9.9° C. and 50 atm, carbon dioxide around 31.0° C. and 72.9 atm, which has a density approximating to that of a liquid and a high diffusion coefficient approximating to that of a gas. Owing to these characteristics, various compounds can be rapidly and efficiently extracted in high yield, and separation of the extractant can be carried out with ease. Furthermore, solubility of various compounds can be largely changed by slightly changing the pressure and temperature, and thus enables selective extraction to be carried out. However, a process for recovering primary normal aliphatic higher alcohols from sugarcane, or products obtained from the sugarcane, or processed products from production of sugar by using a fluid in a subcritical or supercritical state as an extractant has not been disclosed yet.

SUMMARY OF THE INVENTION

An object of the present invention is to recover primary normal aliphatic higher alcohols in an industrially advantageous manner while overcoming the disadvantages of the prior art, and the object of the present invention can be attained according to a process which comprises contacting sugarcane, or products obtained from the sugarcanes, or processed products from production of sugar with a fluid in a subcritical or supercritical state as an extractant, thereby extracting a trace amount of primary normal aliphatic higher alcohols contained in the raw materials as an extract, and separating the extracted alcohols from the extract.

The present inventors have so far extensively studied extraction of various useful components from various natural materials, using a fluid in a subcritical or supercritical state as an extractant.

Taking into account the fact that it has been said for a long time that sugarcane contains useful components, and, for example, when scums, precipitates or filter cakes from the purification process of sugarcane juice are mixed into soil, they have a considerable effect on the growth of crops, and taking the juice squeezed out of sugarcanes is effective for health maintenance, the present inventors have found that, when sugarcanes, or products obtained for the sugarcanes, or processed products from production of sugar is extracted with a fluid in a subcritical or supercritical state as an extractant, primary normal aliphatic higher alcohols such as octacosanol, triacontanol, etc. contained in trace amounts therein can be surprisingly and selectively extracted from the raw material. Furthermore, the present inventors have studied species of raw materials for extraction and extractant, conditions for the extraction and separation, and have established the present invention.

The raw material for extraction in the present invention includes sugarcanes, products obtained from the sugarcanes, and processed products from production of sugar, for example, sugarcanes as such, sugarcane juice obtained by milling or diffusion of sugarcanes, residues or bagasse from milling or diffusion of sugarcanes to obtain sugarcane juice, scums, precipitates or filter cakes from clarification process of sugarcane juice by liming, carbonating, sulfiting, phosphating, etc., clarified sugarcane juice from the liming, molasses and blackstrap, which can be used alone or in their mixture.

Compounds to be extracted from the said raw material in the present invention are primary normal aliphatic higher alcohols having 20 to 36 carbon atoms, and particularly octacosanol and triacontanol from the viewpoint of usefulness.

The fluid in a subcritical or supercritical state for use in the present invention is a fluid approximately at a critical temperature and critical pressure or at higher temperature and pressure than the critical temperature and critical pressure, as described before, i.e. a fluid having a density approximating to that of a liquid and a high diffusion coefficient approximating to that of a gas. In the present invention, generally any fluid can be used, so far as it is in a subcritical or supercritical state, but it is preferable to use carbon dioxide as an extractant owing to many merits such as a distinguished separatability of primary normal aliphatic higher alcohols from the ordinary vegetable oils, applicable treatment at a relatively low temperature, simple handling and operation, economical advantage, etc.

In the present invention, carbon dioxide at a temperature of 25° to 100° C. and a pressure of 60 to 300 kg/cm$^2$G is preferable from the viewpoint of extraction and separation.

In the present invention, at least one organic solvent selected from lower alcohols, aromatic hydrocarbons, aliphatic hydrocarbons, cyclic ethers, and aliphatic ketones can be used as an entrainer for the carbon dioxide as an extractant. The entrainer can increase the ability of carbon dioxide as an extractant. It is preferable to use ethanol as an entrainer because it is used for food and drink.

In the present invention, separation of the extracted alcohols from the extract is carried out at a temperature of 30° to 100° C. and a pressure of 1 to 200 kg/cm$^2$G.

In the present invention, the extraction can be carried out stagewise by changing the extraction pressure with time, or separation of the extracted alcohols from the extract can be fractionally carried out, thereby separating the extracted alcohols into the respective alcohol component fractions.

BRIEF DESCRIPTION OF THE DRAWING

Single FIGURE shows a flow diagram according to one embodiment of the present invention.

PREFERRED EMBODIMENTS OF THE INVENTION

One embodiment of carrying out the present invention will be described in detail below, referring to the flow diagram in the drawing.

In FIGURE, CO$_2$ from a CO$_2$ cylinder 1 is compressed to a predetermined pressure by a compressor 2, passed through a heat exchanger 3 to heat the compressed CO$_2$ to a predetermined extraction temperature in a subcritical or supercritical state, and led to an extractor 4 provided with a heating jacket 10 to adjust the extraction temperature. In the extractor 4, sugarcanes, or products obtained from the sugarcanes, or processed products from production of sugar are charged as raw material and contacted with the CO$_2$ to make extraction. Then, the CO$_2$ phase containing the extracted components as an extract is passed through a pressure-reducing valve 5 and led to a separator 6 provided with a heating jacket 11 to adjust the separation temperature, where the extracted components are separated from the CO$_2$. The CO$_2$ separated from the extracted component is cooled and liquefied in a condensor 7 and recycled to the compressor 2. When an entrainer is used, the entrainer can be mixed into the raw material in advance, and then the raw material is charged into the extractor 4, or a predetermined amount of an entrainer from an entrainer holder 8 is led to the heat exchanger 3 by a pump 9. When the extractant is used experimentally in one way, the amount of discharged gas is controlled by a flow rate integrator 12 and a flow meter 13. In the extractor 4, the extraction must be carried out under a CO$_2$ pressure of 50 to 500 kg/cm$^2$G, preferably 60 to 300 kg/cm$^2$G, and an extraction temperature of 25° to 100° C., preferably 25° to 70° C. At too low CO$_2$ pressure and extraction temperature, CO$_2$ is in a liquid state and an energy is required also for the separation of the extractant from the extract, whereas at too high CO$_2$ pressure and extraction temperature, the equipment cost is so increased that there will be an economical problem, and also an adverse effect such as heat deterioration, etc. will appear.

In the separator 6, a better result can be obtained when the extracted components are separated from CO$_2$ at a pressure of 1 to 200 kg/cm$^2$G and a temperature of 30° to 100° C.

It is possible to lead the extractant to the extractor 4 while increasing the pressure of the extracting agent stagewise with time to conduct stagewise extraction. Furthermore, a plurality of extractors can be provided in parallel to conduct semi-continuous operation by switching one extractor to another. The separation of the extracted components from the extractant is usually carried out by pressure reduction with time as described above, but the separation can be carried out by changing the temperature with time, because the solubility is decreased with increasing extraction temperature.

Generally, in the process shown in Single FIGURE, the extracted components are separated from the extractant in the separator 6 under a constant pressure throughout the operation, but the extracted components can be fractionated by reducing the pressure stagewise with time. By stagewise reduction of pressure with time, octacosanol or triacontanol can be obtained as enriched, for example, to about 10 times the concentration of octacosanol or triacontanol obtained when the separation is carried out under a constant pressure throughout the operation. That is, the desired components can be recovered at high concentrations by the fractionation based on the separation under varied pressures with time. It is also possible to provide a plurality of separators in series to conduct fractional separation and recovery of extracted components by stagewise reduction of the pressure with time.

The present invention will be described in detail below, referring to Examples, which will not be limitative of the present invention.

EXAMPLE 1

Sugarcane juice obtained by milling sugarcanes was heated, and subjected to a lime-clarifying process. The resulting precipitates were filtered, and the filter cakes were dried. 350 g of the thus obtained dried filter cakes were extracted with supercritical $CO_2$ at the constant temperature of 40° C. and under the constant pressure of 230 kg/cm$^2$G as an extractant through the operation according to the process of Single FIGURE, and the extracted components were separated from $CO_2$ at room temperature under the atmospheric pressure, whereby 15 g of the extracted components were obtained. It was found by analysis that 8.5% by weight of octacosanol was contained in the extracted components.

EXAMPLE 2

2 kg of the same dried filter cakes as used in Example 1 were extracted with supercritical $CO_2$ at varied temperatures of 38° to 41° C. under varied pressures of 200 to 250 kg/cm$^2$G with time as an extractant according to the process of Single FIGURE, and the extracted components were separated from $CO_2$ at room temperature under the atmospheric pressure throughout the operation, whereby 24 g of fraction (I), 25 g of fraction (II) and 22 g of fraction (III), total 71 g of extracted components, were obtained. It was found by analysis that contents of octacosanol and triacontanol in the respective fractions were as given in the following Table.

TABLE

|  | Octacosanol (wt. %) | Triacontanol (wt. %) |
|---|---|---|
| (I) | 7.8% | 0.49% |
| (II) | 8.6% | 0.68% |
| (III) | 10.1% | 0.84% |

EXAMPLE 3

1.8 kg of the same filter cakes as used in Example 1 was extracted with $CO_2$ at the constant temperature of 39° C. under the constant pressure of 240 kg/cm$^2$G as an extractant according to the process of Single FIGURE, and the extracted components were separated at a constant temperature of 35° C. under a pressure of 140 kg/cm$^2$G throughout the operation, whereby 12 g of white powder was obtained. It was found by analysis that 61% by weight of octacosanol and 4.3% by weight of triacontanol were contained in the white powder.

EXAMPLE 4

200 g of dried rinds whittled away from sugarcanes were extracted with supercritical $CO_2$ as an extractant at varied temperatures of 38° to 40° C. under varied pressures of 230 to 250 kg/cm$^2$G according to the process of Single FIGURE, and the extracted components were separated from $CO_2$ at room temperature under the atmospheric pressure, whereby 17 g of extracted components were obtained. It was found by analysis that 36% by weight of octacosanol, 2.8% by weight of triacontanol and 9.3% by weight of octacosanol were contained in the extracted components.

EXAMPLE 5

5 kg of dried and milled sugarcanes was extracted with supercritical $CO_2$ at varied temperatures of 38° to 40° C. under varied pressures of 220 to 250 kg/cm$^2$G with time as an extractant according to the process of Single FIGURE, and the extracted components were separated from $CO_2$ at room temperature under the atmospheric pressure throughout the operation, whereby 6.8 g of extracted components were obtained. It was found by analysis that 3.2% by weight of octacosanol was contained in the extracted components.

EXAMPLE 6

2.5 kg of pressed cakes (bagasse) by-produced when sugarcane juice was obtained by milling the sugarcanes were extracted with supercritical $CO_2$ at varied temperatures of 39° to 41° C. with time under a constant pressure of 220 kg/cm$^2$G as an extractant according to the process of Single FIGURE, and the extracted components were separated from $CO_2$ at room temperature under the atmospheric pressure throutghout the operation, whereby 4.3 g of extracted components were obtained. It was found by analysis that 5.2% by weight of octacosanol was contained in the extracted components.

EXAMPLE 7

3 kg of molasses by-produced in the process for producing sugarcane were extracted with supercritical $CO_2$ as an extractant at varied temperatures of 38° to 41° C. under varied pressures of 200 to 230 kg/cm$^2$G with time and the extracted components were separated from $CO_2$ at room temperature under the atmospheric pressure throughout the operation according to the process of Single FIGURE, whereby 1.9 g of the extracted components were obtained. It was found by analysis that 5.1% by weight of octacosanol was contained in the extracted components.

EXAMPLE 8

100 g of sugarcane wax obtained by extraction of the same dried filter cakes as used in Example 1 with n-hexane, followed by removal of n-hexane from the extract was extracted with $CO_2$ as an extractant at a constant temperature of 40° C. under a constant pressure of 230 kg/cm$^2$G and the extracted components were separated from $CO_2$ at the constant temperature of 40° C. under the constant pressure of 150 kg/cm$^2$G of throughout the operation according to the process of Single FIGURE, whereby 4.6 g of white powdery extracted components were obtained. It was found by analysis that 59% by weight of octacosanol and 3.8% by weight of triacontanol were contained in the extracted components.

EXAMPLE 9

Extraction was carried out in the same manner under the same conditions as in Example 1, except that 1% by weight of ethanol was added to $CO_2$ on the basis of $CO_2$, whereby 18 g of the extracted components were obtained. It was found by analysis that 9.8% by weight of octacosanol was contained in the extracted components.

According to the present invention, useful primary normal aliphatic higher alcohols such as octacosanol, triacontanol, etc. can be recovered from sugarcanes, or whereby 18 g of the extracted components were obtained. It was found by analysis that 9.8% by weight of octacosanol was contained in the extracted components.

According to the present invention, useful primary normal aliphatic higher alcohols such as octacosanol, triacontanol, etc. can be recovered from sugarcanes, or products obtained from the sugarcanes or processed products from production of sugar as an extraction raw material in an industrially advantageous manner with the following distinguished effects as compared with the prior art.

(1) No example of recovering the higher alcohols from such an extraction raw material with a high extraction efficiency has been disclosed yet, and the present invention provides an epoch-making process for recovering the higher alcohols at high concentrations from wastes from the lime-clarifying process, such as precipitates (2) No impurities such as heavy metals, aquicultural chemicals, etc. are extracted as extracted components in the extraction step. That is, the extracted components contain no such impurities.

(3) The present process is simple in steps and can perform selective fractionation with a high efficiency.

(4) Extraction is carried out at a relatively low temperature in an inert atmosphere, and thus there is no change in quality of the extracted components.

(5) The present process is economically distinguished particularly from the viewpoint of energy consumption.

(6) A large amount of an organic solvent is not used, and thus there are no problems at all of operational danger, environmental pollution, contamination of extracted components and raffinate, etc.

We claim:

1. A process for recovering primary normal aliphatic higher alcohols having 20 to 36 carbon atoms, which comprises contacting sugarcanes, or products obtained from the sugarcanes, as an extraction raw material with a fluid in a subcritical or supercritical state being at least at about its critical temperature and about its critical pressure as an extractant, thereby extracting a trace amount of primary normal aliphatic higher alcohols having 20 to 36 carbon atoms contained in the extraction raw materials as an extract and separating the extracted alcohols from the extract.

2. A process according to claim 1, wherein the extraction raw material is at least one of sugarcanes as such, sugarcane juice obtained by milling or diffusion of sugarcanes, residues or bagasses from milling or diffusion of sugarcanes to obtain sugarcane juice, scums, precipitates or filter cakes from clarification process of sugarcane juice by liming, carbonating, sulfiting or phosphating, clarified sugarcane juice from the liming, and molasses.

3. A process according to claim 1, wherein the fluid in a subcritical or supercritical state is carbon dioxide.

4. A process according to claim 1, wherein the fluid in a subcritical or supercritical state is carbon dioxide at a temperature of 25° to 100° C. under a pressure of 60 to 300 kg/cm$^2$G.

5. A process according to claim 1, wherein at least one organic solvent selected from lower alcohols, aromatic hydrocarbons, aliphatic hydrocarbons, cyclic ethers, and aliphatic ketones is used as an entrainer to the extractant.

6. A process according to claim 5, wherein the entrainer is ethanol.

7. A process according to claim 1, wherein the separation of the extracted alcohols from the extract is carried out at a temperature of 30° to 100° C. under a pressure of 1 to 200 kg/cm$^2$G.

8. A process according to claim 1, wherein the extraction is carried out stagewise by changing the extraction pressure with time.

9. A process according to claim 1, wherein the separation of the extracted alcohols from the extract is fractionally carried out, thereby separating the extracted alcohols into the respective alcohol component fractions.

10. A process according to claim 1, wherein the primary normal aliphatic higher alcohols are at least one of octacosanol and triacontanol.

11. The process of claim 2 wherein said molasses is blackstrap.

12. The process of claim 1 wherein said fluid is at higher temperature and pressure than its critical temperature and critical pressure.

13. The process of claim 1 wherein said products obtained from sugarcanes are processed products from production of sugar.

14. A process according to claim 3, wherein at least one organic solvent selected from lower alcohols, aromatic hydrocarbons, aliphatic hydrocarbons, cyclic ethers, and aliphatic ketones is used as an entrainer to the extractant.

15. A process according to claim 14, wherein the entrainer is ethanol.

* * * * *